(12) United States Patent
Rushing et al.

(10) Patent No.: US 6,222,176 B1
(45) Date of Patent: *Apr. 24, 2001

(54) DIGITAL DENSITOMETER WITH LUT OUTPUT SUMMATION TO YIELD DENSITY VALUE

(75) Inventors: Allen J. Rushing, Webster; William A. Hameister, Penfield, both of NY (US)

(73) Assignee: NexPress Solutions LLC, Rochester, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/185,842

(22) Filed: Nov. 4, 1998

(51) Int. Cl.$^7$ ....................................................... H01J 40/14
(52) U.S. Cl. ..................................... 250/214 AG; 347/184
(58) Field of Search ........................... 250/205, 559.02, 250/214 AG, 559.28; 356/443; 347/251, 184; 399/59

(56) References Cited

U.S. PATENT DOCUMENTS

| | | |
|---|---|---|
| 4,473,029 | 9/1984 | Fritz et al. .............................. 399/236 |
| 4,546,060 | 10/1985 | Miskinis et al. ....................... 430/108 |
| 4,550,254 | 10/1985 | Zomorrodi et al. .................. 250/338.1 |
| 4,673,807 | 6/1987 | Kobayashi et al. ............. 250/214 AG |
| 5,065,234 | * 11/1991 | Hung et al. ................................ 358/80 |
| 5,117,119 | 5/1992 | Schubert et al. ................. 250/559.02 |
| 5,649,266 | 7/1997 | Rushing ................................... 399/59 |

* cited by examiner

*Primary Examiner*—Que T. Le
*Assistant Examiner*—Thanh X. Luu
(74) *Attorney, Agent, or Firm*—James D. Leimbach

(57) ABSTRACT

An auto-ranging densitometer includes a photodetector and an amplifier circuit adapted to produce an output signal proportional to intensity of light on the photodetector. The amplifier circuit has multiple gains that successively increase. An analog to digital converter converts the output signal of the amplifier circuit to digital format. A gain select logic outputs a gain code used to select the gain of the amplifier. A density signal generator circuit includes two LUTs, one of the LUTs being adapted to receive the output of the analog to digital converter and produce an output density scaled to include only low order bits; and the other of the LUTs being to receive the gain code and produce an output density scaled to include only high order bits. The outputs of the two LUTs are concatenation added to produce a summation density signal.

16 Claims, 6 Drawing Sheets

| A/D MSB (MOST SIGNIFICANT BIT) | A/D OTHER BITS | PRESENT GAIN | U/D COUNTER OPERATION |
|---|---|---|---|
| 0 | X (DON'T CARE) | <MAX GAIN | COUNT UP (TO NEXT HIGHER GAIN) |
| 0 | X | =MAX GAIN | INHIBIT (OVERRIDES U/D COMMAND) NO GAIN CHANGE |
| 1 | ALL=1 (SATURATED) | >MIN GAIN | COUNT DOWN (TO NEXT LOWER GAIN) |
| 1 | ALL=1 (SATURATED) | =MIN GAIN | INHIBIT NO GAIN CHANGE |
| 1 | AT LEAST ONE BIT=0 | X | INHIBIT NO GAIN CHANGE |

FIG. 4

| A/D COUNT | PRESENT GAIN | U/D COUNTER OPERATIO |
|---|---|---|
| <=UPWARD SWITCH THRESHOLD | <MAX GAIN | COUNT UP (TO NEXT HIGHER GAIN) |
| <=UPWARD SWITCH THRESHOLD | =MAX GAIN | INHIBIT NO GAIN CHANGE |
| > UPWARD SWITCH THRESHOLD, NOT SATURATED | X | INHIBIT NO GAIN CHANGE |
| SATURATED | >MIN GAIN | COUNT DOWN (TO NEXT LOWER GAIN) |
| SATURATED | =MIN GAIN | INHIBIT NO GAIN CHANGE |

FIG. 6

DIGITAL DENSITOMETER WITH LUT OUTPUT SUMMATION TO YIELD DENSITY VALUE

CROSS REFERENCE TO RELATED APPLICATIONS

Reference is made to commonly assigned, co-pending U.S. Patent application Ser. No. 09/183,509, entitled DIGITAL DENSITOMETER USING VOLTAGE-CONTROLLED OSCILLATOR, COUNTER, AND LOOKUP TABLE, filed in the name of A. Rushing, and Ser. No. 09/182,912 entitled DIGITAL DENSITOMETER COMBINING AUTO-RANGING WITH CIRCUITRY FOR EXPONENTIAL DECAY, COMPARISON TO A THRESHOLD, AND AN UP-DOWN COUNTER, filed our names, and Ser. No. 09/185,926 entitled DIGITAL DENSITOMETER WITH AUTO-RANGING, filed in our names concurrently herewith.

FIELD OF THE INVENTION

The present invention relates to density measurement devices and methods, and is particularly useful in imaging devices such as for example in electrostatographic reproduction apparatus.

BACKGROUND OF THE INVENTION

In the field of light measurement and densitometry, the need to convert from an electrical voltage proportional to light intensity to another signal proportional to optical density has long been recognized. One approach in the prior art has been to obtain a sensor voltage signal representing intensity of transmitted or reflected light and convert this analog signal to digital form. The digital value is then used to enter a stored LUT of intensity and density values. The digital density value corresponding to the digital intensity value is read from the LUT.

U.S. Pat. No. 5,117,119 discloses an automatic gain selection electronic circuit, along with a second LUT to obtain high accuracy and resolution over an increased range of large densities. The first (or "base") LUT contains density values corresponding to an analog-to-digital converter output for the lowest gain. The second (or "range") LUT is much smaller than the first LUT and contains the relative density corresponding to each available gain. It provides the additional density output associated with the gain selected. The two LUT outputs are summed to obtain the actual density measurement.

The three ranges illustrated in U.S. 5,117,119 are divided by two threshold values in a 10:1 ratio. Thus two ranges have 10:1 max-to-min light or voltage input ratios, and the third range (used for lowest light intensities or highest density) may have arbitrarily small input light or voltage level. The illustration in U.S. Pat. No. 5,117,119 shows accuracy of 0.01 density units, but requires a 10-bit analog-to-digital converter to do so. In turn, the 10-bit analog-to-digital converter requires a large "base" LUT of $2^1$=01024 entries. A major limiting factor in accuracy is the analog-to-digital converter resolution. Worst-case density resolution for each range comes at the high-density (low light intensity) end of the range, where the analog-to-digital converter resolution, i.e., one count, corresponds to the largest density increment. U.S. Pat. No. 5,117,119 uses multiple analog threshold voltage levels for comparison to the light sensor voltage signal. Low levels of electrical noise and circuit variability could degrade the comparator accuracy and reliability for the low-voltage thresholds.

SUMMARY OF THE INVENTION

It is an object of the present invention to use more but smaller gain ranges (roughly 2:1 ranges in a preferred embodiment) and a particular scaling of the LUT density output that simplifies the summation of the "range" and "base" LUT outputs.

It is another object of the present invention to provide an improved automatic gain selection circuitry and a particular scaling of the LUT density output that simplifies the summation of the "range" and "base" LUT outputs.

It is yet another object of the present invention to provide the option to use "overlapping" nominal density ranges with hysteresis in the gain selection circuitry and a particular scaling of the LUT density output that simplifies the summation of the "range" and "base" LUT outputs.

According to a feature of the present invention, an auto-ranging densitometer includes a photodetector and an amplifier circuit adapted to produce an output signal proportional to intensity of light on the photodetector. The amplifier circuit has multiple gains that successively increase. An analog to digital converter converts the output signal of the amplifier circuit to digital format. A gain select logic outputs a gain code used to select the gain of the amplifier. A density signal generator circuit includes two LUTs, one of the LUTs being adapted to receive the output of the analog to digital converter and produce an output density scaled to include only low order bits; and the other of the LUTs being to receive the gain code and produce an output density scaled to include only high order bits. The outputs of the two LUTs are concantenation added to produce a summation density signal.

BRIEF DESCRIPTION OF THE DRAWINGS

The subsequent description of the preferred embodiments of the present invention refers to the attached drawings wherein:

FIG. 4 is a truth table defining the gain select and counter logic for two described embodiments.

FIG. 6 is a truth table defining the gain select and counter logic for the embodiment of FIG. 5.

DETAILED DESCRIPTION OF THE INVENTION

Because apparatus of the general type described herein are well known the present description will be directed in particular to elements forming part of, or cooperating more directly with, the present invention. While the invention will be described with reference to imaging apparatus and particularly to an electrophotographic system, the invention can also be used in other imaging apparatus and in environments not in the imaging field.

Figure 1:
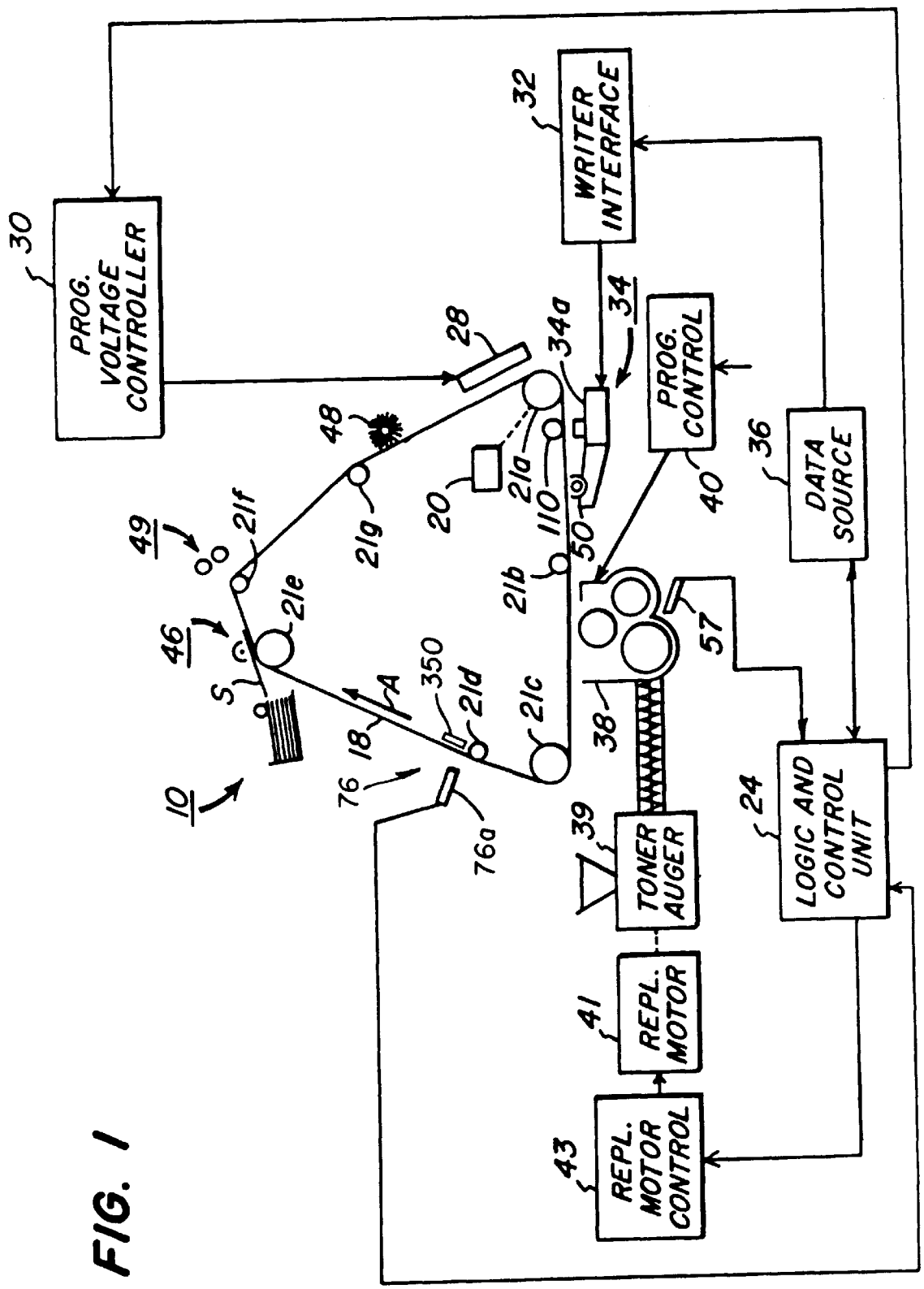
FIG. 1 is a side elevational view in schematic form of an electrostatographic apparatus that is used in accordance with a preferred embodiment of the invention.

With reference to the electrophotographic copier and/or printer machine 10 as shown in FIG. 1, a moving recording member such as photoconductive belt 18 is entrained about a plurality of rollers or other supports 21a–21g one or more of which are driven by a motor 20 so as to advance the belt in a direction indicated by an arrow "A" past a series of work stations of machine 10. A logic and control unit 24, which has a digital computer, has a stored program for sequentially actuating the work stations in response to signals from various sensors and encoders, as is well known.

A primary charging station 28 sensitizes belt 18 by applying a uniform electrostatic charge of predetermined primary voltage $V_0$ to the surface of the belt. The output of the charging station is regulated by a programmable voltage controller 30, which is in turn controlled by logic and control unit 24 to adjust primary voltage $V_0$ for example through control of electrical potential ($V_{grid}$) to a grid that controls movement of corona charges from charging wires to the surface of the recording member, as is well known. Other known forms of chargers, including roller chargers, may also be used.

At an exposure station 34, projected light from a write head 34a dissipates the electrostatic charge on the photoconductive belt to form a latent image of a document to be copied or printed. The write head preferably has an array of light-emitting diodes or other light source such as a laser or other spatial light modulator for exposing the photoconductive belt picture element (pixel) by picture element with a regulated intensity and exposure, $E_o$. Alternatively, the exposure may be by optical projection of an image of a document or a patch onto the photoconductor.

Where a light-emitting diode or other electro-optical exposure source or writer is used, image data for recording is provided by a data source 36 for generating electrical image signals. The data source 36 may be a computer, a document scanner, a memory, a data network, etc. Signals from the data source and/or logic and control unit may also provide control signals to a writer interface 32 for identifying exposure correction parameters in, for example, a lookup table (LUT) for use in controlling image density. Travel of belt 18 brings the areas bearing the latent charge images into a development station 38. The development station has one (more if color) magnetic brushes in juxtaposition to, but spaced from, the travel path of the belt. Magnetic brush development stations are well known. For example, see U.S. Pat. No. 4,473,029 to Fritz et al and U.S. Pat. No. 4,546,060 to Miskinis et al. Other types of development stations may be used as is well known and plural development stations may be provided for developing images in plural colors or with toners of different physical characteristics.

Logic and control unit 24 selectively activates the development station in relation to the passage of the image areas containing latent images to selectively bring the magnetic brush into engagement with or a small spacing from the belt. The charged toner particles of the engaged magnetic brush are attracted imagewise to the latent image pattern to develop the pattern.

Conductive portions of the development station, such as conductive applicator cylinders, act as electrodes. The electrodes are connected to a variable supply of D.C. potential VB regulated by a programmable controller 40. Details regarding the development station are provided as an example, but are not essential to the invention.

A transfer station 46 as is also well known is provided for moving a receiver sheet "S" into engagement with the photoconductive belt in register with the image for transferring the image to a receiver. Alternatively, an intermediate member may have the image transferred to it and the image may then be transferred to the receiver. A cleaning station 48 is also provided subsequent to the transfer station for removing toner from the belt 18 to allow reuse of the surface for forming additional images. In lieu of a belt, a drum photoconductor or other structure for supporting an image may be used. After transfer of the unfixed toner images to a receiver sheet, such sheet is detacked from the belt and transported to a fuser station 49 where the image is fixed.

The logic and control unit provides overall control of the apparatus and its various subsystems as is well known. Programming commercially available microprocessors is a conventional skill well understood in the art.

Figure 2:
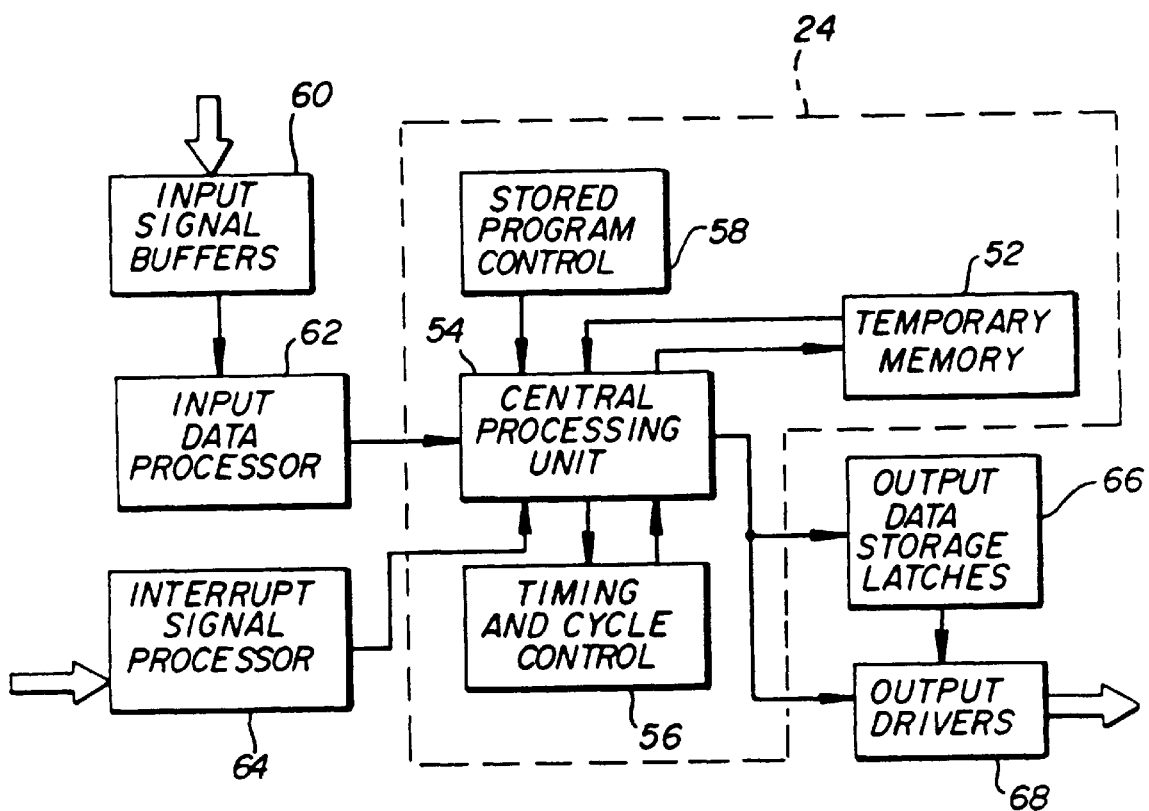
FIG. 2 is a block diagram of a logic and control unit for controlling the apparatus of FIG. 1.

Referring to FIG. 2, a block diagram of a typical logic and control unit 24 is shown. The logic and control unit comprises temporary data storage memory 52, central processing unit 54, timing and cycle control unit 56, and stored program control 58. Data input and output is performed sequentially through or under program control. Input data are applied either through input signal buffers 60 to an input data processor 62 or through an interrupt signal processor 64. The input signals are derived from various switches, sensors, and analog-to-digital converters that are part of the apparatus 10 or received from sources external to machine 10.

The output data and control signals are applied directly or through storage latches 66 to suitable output drivers 68. The output drivers are connected to appropriate subsystems.

Process control strategies generally utilize various sensors to provide real-time control of the electrostatographic process and to provide "constant" image quality output from the user's perspective.

One such sensor may be a densitometer 76 to monitor development of test patches in non-image areas of photoconductive belt 18, as is well known in the art. See for example U.S. Pat. No. 5,649,266. The densitometer is intended to insure that the transmittance or reflectance density of a toned patch on the belt is maintained. The densitometer may be comprised of an infrared light-emitting diode 76a which shines light through the belt or is reflected by the belt onto a photodiode 350. The photodiode generates an electrical signal which varies directly with the flux of light received. The signal is to be converted to a density value reading. In the case of transmission density, this density value is reduced by the density value of a bare patch, to give a signal, $D_{out}$, representative of an estimate of toned density. The $D_{out}$, signal may be used to adjust process parameters $V_0$, $E_0$, or $V_B$. The $D_{out}$, signal may also be used to assist in the maintenance of the proper concentration of toner particles in the developer mixture by having the logic and control unit provide control signals to a replenisher motor control 43. Replenisher motor control 43 controls replenisher motor 41 that in turn drives a toner auger 39 for feeding new toner particles into development station 38. A toner concentration monitor probe 57 provides signals to the logic and control unit about relative concentration of toner particles to carrier particles in the developer mix.

A second sensor useful for monitoring process parameters is an electrometer probe 50 which is mounted at a location preferably downstream of the corona charging station 28 relative to the direction of the movement of the belt 18 which direction is indicated by the arrow A. In the example illustrated in FIG. 1 the electrometer probe 50 is mounted immediately downstream of the writehead 34a.

Figure 3:
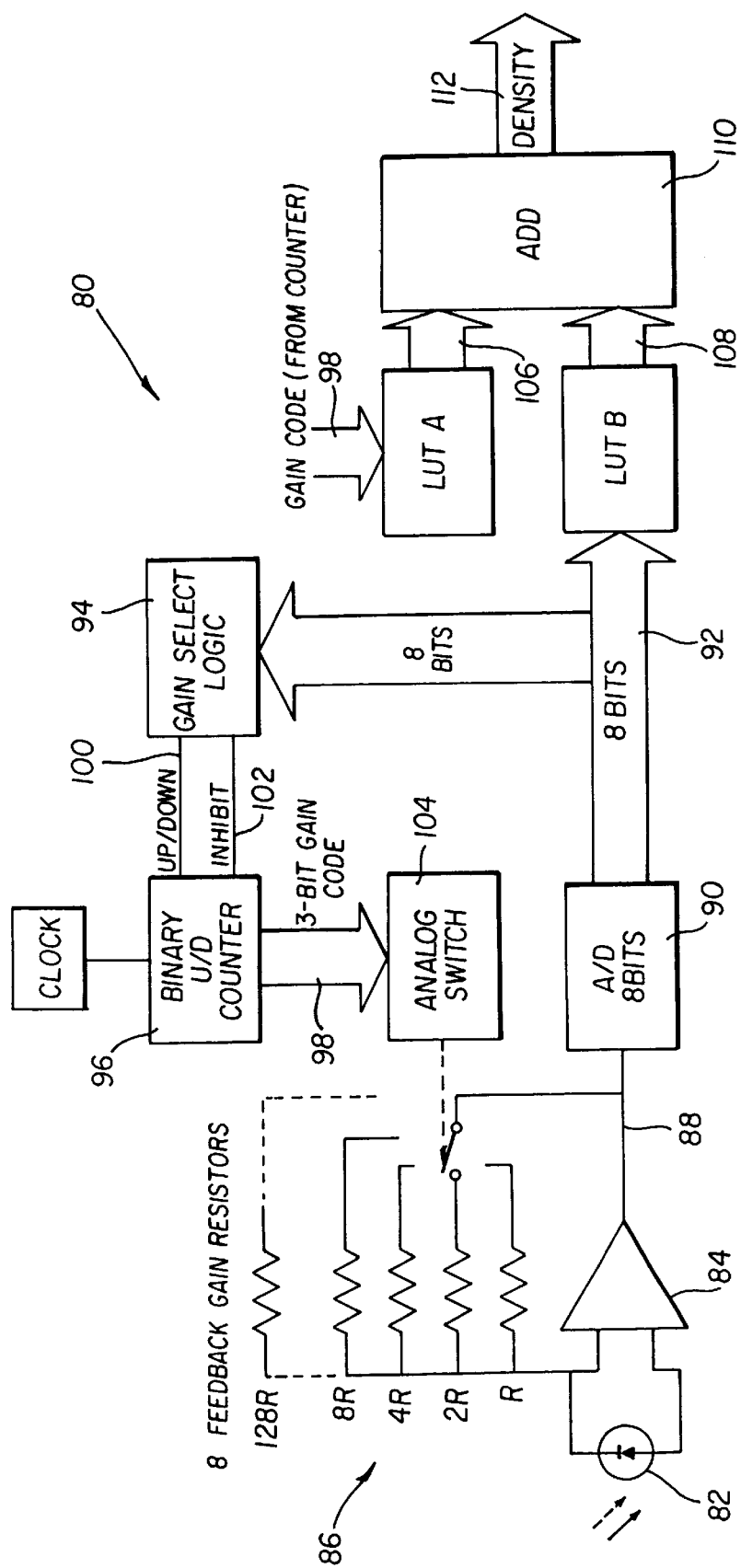
FIG. 3 is a block diagram of a densitometer according to a preferred embodiment of the present invention.

Referring to FIG. 3, an auto-ranging digital densitometer 80 according to a preferred embodiment of the present invention includes a conventional photodiode detector 82 to provide a current output into an amplifier 84. A variable feedback resistor system 86 around amplifier 84 provides a determinable gain so that the amplifier output voltage signal 88 is proportional to the photocontent in photodiode detector 82. Feedback resistor system 86 is programmable in real time to accommodate a wide range of light intensities, as explained below. Output signal 88 is inputted into an analog-to-digital converter 90 to produce a digital signal 92 of, say, eight bits.

The binary value of signal 92 is inputted to gain select logic 94, the outputs of which goes to a binary up/down counter 96 with a 3-bit output 98. Counter 96 is driven up or down according to the table of FIG. 4. One gain select logic output 100 controls the up or down direction of counter 96, and the other output 102 inhibits the count when digital signal 92 has been driven to a desired range.

The 3-bit count output 98 of counter 96 serves as a code for an analog switch 104 to select one of eight resistors of variable feedback resistor system 86 to provide a high level of sensitivity without saturation. That is, desensitization of the amplifier is desirable in response to increased light input to prevent driving the system into saturation. On the other hand, one would not want the gain to be so low as to produce poor resolution. By using a variable or programmable gain, good densitometer resolution is attainable over a large range of densities.

The same 3-bit gain code is sent from counter 96 to a look-up table "A" indicating the specific resistor which has been selected. Look-up table "A" is very small, having a number of rows only equal to the number of feedback resistors of variable feedback resistor system 86; and there is a distinct "range" density value associated with each row of look-up table "A" provided to an output 106. As the gain of amplifier 84 is increased by gain select logic 94, more value is added to "range" density value output 106 of look-up table "A" to compensate and account for the gain change. Conventional EEPROM (electrically erasable programmable read-only memory) IC's are preferred for the LUT's. They are easily programmed initially, and individually customized according to resistor tolerance if necessary.

A look-up table "B" is larger than look-up table "A" as it needs as many rows as there are output states of analog-tdigital converter 90. For example, if analog-to-digital converter 90 is 8 bit, there will be 256 rows in look-up table "B". The output 108 of the two look-up table "B" is a density value that is added (or otherwise combined) at 110 to the output 106 of LUT "A" to provide a density signal 112 characteristic of an overall density.

In general, circuitry need be provided that deals with all the digits in the two numbers that are being added. However with particular gain values and output density scaling, the operation of addition reduces to a mere concatenation of digits. With this simplification, the low-order and high-order output digits are segregated in the "base" and "range" LUT's, respectively. The digits are binary digits in the preferred ernbodiment, but may be in other number bases, such as decimal. With this simplification, one can get along with a concatenation rather than an actual addition.

The density is scaled in the LUT's such that the binary representation over the fill range of the "base" LUT is 2N1, e.g. 00000 to 11111. The "base" LUT thus provides the N low-order bits of the density value, while the "range" LUT provides the high-order bits of the density value. The summation of the 2 LUT outputs then becomes simply the concatenation of the high-order bits from the "range" LUT and the low-order bits from the "base" LUT, and no actual adder circuit or algorithm is required. For example, "range" LUT output of "HHHxxxxx" is concatenated with "base" LUT output of "xxxLLLLL" to yield a 8-bit density value of "HHHLLLLL", where "H" denotes a high-order bit, "L" denotes a low-order bit, and "x" is a mere placeholder.

In a preferred embodiment as in FIG. 3, there is an approximately 2:1 ratio in the successive feedback resistors as opposed to the 10:1 ratio that is disclosed in U.S. Pat. No. 5,117,119. A 2:1 ratio provides amore uniform distribution of resolution error, which in turn permits a lower cost analog to digital converter and a smaller look-up table without loss of accuracy in the end result. It is the nature of converting from transmittance space to density space that, if there exists a fixed resolution across the entire range of transmittance space, upon conversion to density space there will be good resolution at one end of the range and poor resolution at the other end. If you have to span a 10:1 range of transmittance, the corresponding resolution in density space varies greatly from very good at one end of the range to very poor at the other end. However, if we change the ratio of resistors from 10:1 to 2:1, for each range we have only a 2:1 range of transmittance. Now, while the corresponding variation in resolution in density space is still non-uniform, it is much less non-uniform then when we had to span a 10:1 range. This permits the use of a less expensive analog to digital converter with fewer bits, and further permits the use a smaller look up table.

Figure 5:
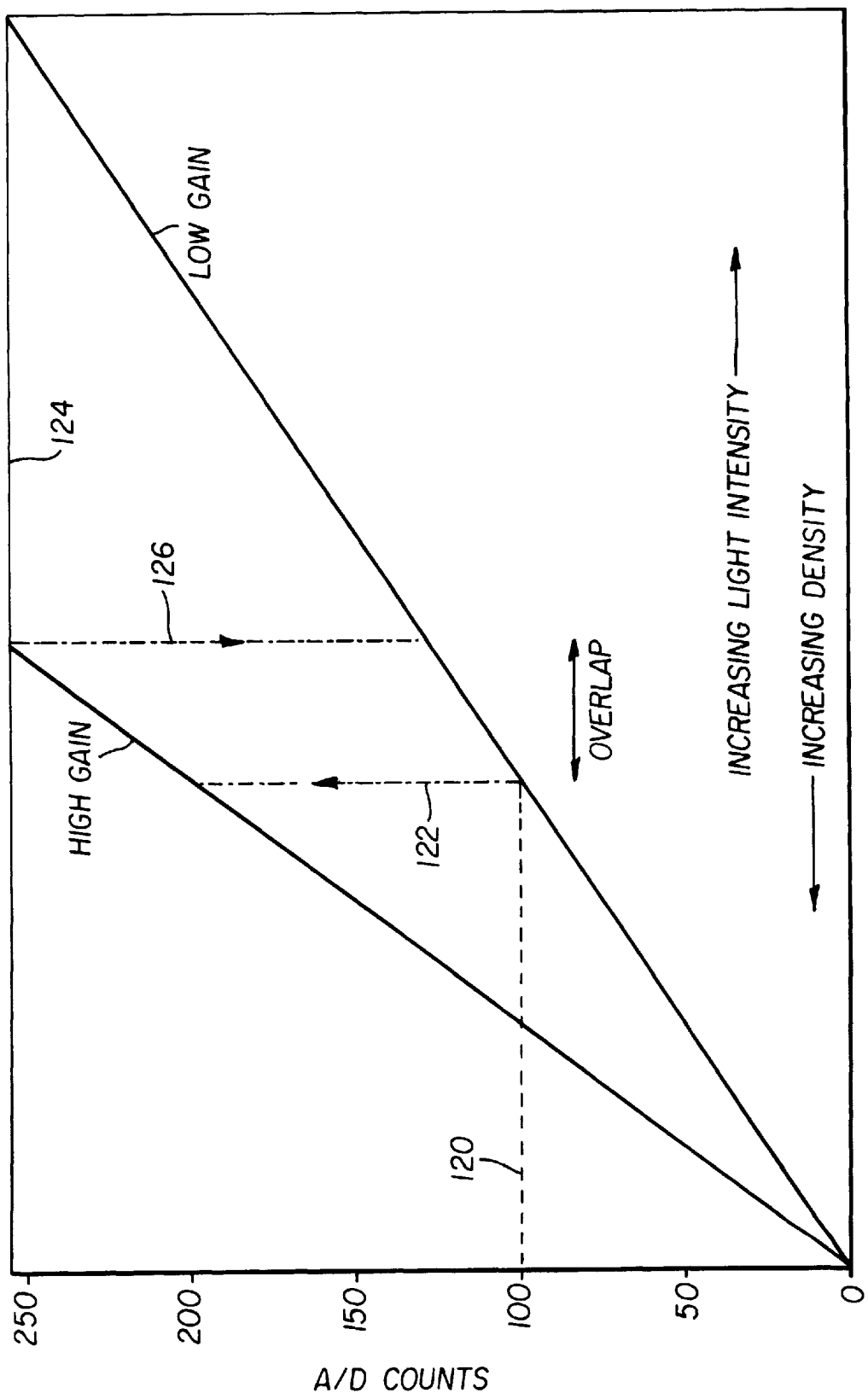
FIG. 5 is a graph of the switching characteristics between two overlapping ranges of another described embodiment.

Another preferred embodiment to which FIG. 3 applies also uses a 2:1 ratio of feedback resistors, but gain select logic 94 is, in this embodiment, designed with hystersis in the switching characteristic (see FIG. 5). FIG. 5 illustrates the gain switching characteristics between just two adjacent ranges referred to on the graph as the "high gain" and "low gain" ranges. The exact slopes (i.e., gains) of the "high gain" and "low gain" characteristics would depend on the amplifier feedback resistance 86. As density increases and the analog to digital converter count 92 decreases to an upward switching threshold 120 where the next higher gain is switched in along path 122, the analog to digital converter count after switching is generally less than the maximum analog to digital converter count 124. The corresponding "base" LUT output is not zero density, but rather a value progranuned according to the actual amplifier feedback resistance for this gain. If density then decreases (analog to digital converter count increases), the next lower gain is not switched in along path 126 until reaching the maximum analog to digital converter count 124, where the "base" LUT density output is zero. Thus the density values corresponding to analog to digital converter counts between the two (upward-going and downward-going) gain switching thresholds are covered by both ranges, so the ranges are said to "overlap". Without such overlap, gain resistor tolerance (inaccuracy) causes two problems. The first problem is a need to adjust the analog to digital converter count-to-density relationship (which can be done in the LUT's). The second problem is a saturated analog to digital converter count at the high-voltage (low-density) end of one or more ranges (not correctable in the LUT's).

Unfortunately, this embodiment of the invention produces programmed corrections for resistor tolerance resulting in high-order and low-order density bits which are not segregated in "base" and "range" LUT's. Therefore the embodiment is incompatible with the concatenation advantage of previously-described embodiments. This provides slight overlap of adjacent ranges, allowing some tolerance on the actual resistor values. Although providing overlap will improve performance of even very precise resistors, it is particularly useful with less precise resistors. For example, an overlap of at least about 0.02 density units will accommodate a 5% resistance error. In U.S. Pat. No. 5,117,119, it would be very important to have very precise resistors so that there are no gaps and no errors in the ranges that need to be covered. In that patent, it would be a problem if the actual resistance is say 5% different than the nominal resistance one is counting on. In this other preferred embodiment of the present invention, for these ranges have been arranged to overlap so if there is variation in these resistors, up to a point, gaps don't end up in the density that can be covered. The logic can be designed in a fixed way. There would be overlap areas for certain light levels where you could select one or the other of the gains, and regardless of which you select you still end up getting valid output from the look up table.

The invention has been described in detail with particular reference to certain preferred embodiments thereof, but it will be understood that variations and modifications can be effected within the spirit and scope of the invention.

What is claimed is:

1. An auto-ranging densitometer for determining the density of a test sample, said densitometer comprising:
    a photodetector that generates an electrical signal in response and proportional to incident light;
    an amplifier circuit adapted to produce an output signal proportional to the electrical signal, the amplifier circuit having multiple gains that successively increase;
    an analog to digital converter adapted to convert the output signal of the amplifier circuit to digital format;
    a gain select logic circuit to output a gain code to select the amplifier gain; and
    a density signal generator circuit including two LUTs, wherein the gain code is used to address the LUTs one of the LUTs is adapted to receive the out put of the analog to digital converter and produce an output density scaled to include only low order bits; and the other LUT is adapted to receive the gain code and produce a output density scaled to include only high order bits, and a concatenation adder of the outputs of the two LUTs to produce a summation density signal.

2. An auto-ranging densitometer as set forth in claim, wherein the multiple gains successively increase in an approximately 2:1 ratio increment.

3. An auto-ranging densitometer as set forth in claim 1 wherein the gain select login circuit is operable in response to the output of the analog to digital converter.

4. The auto-ranging densitometer of claim 1 wherein the density signal generator further comprises the LUTs having both the output of the analog to digital converter and the gain of the amplifier used as an address for the LUTs.

5. The auto-ranging densitometer of claim 4 wherein the address has a number of bits equal to a summation of the output of the analog to digital converter and the gain of the amplifier.

6. The auto-ranging densitometer of claim 4 wherein the LUTs have an output that is combined.

7. The auto-ranging densitometer of claim 4 wherein the output from the LUTs is a concatenation of both outputs from the LUTs.

8. The auto-ranging densitometer of claim 4 further comprising wherein the output from the LUTs is an addition of both outputs from the LUTs.

9. An auto-ranging densitometer for determining the density of a test sample, said densitometer comprising:
    a photodetector that generates an electrical signal in response and proportional to incident light;
    an amplifier circuit adapted to produce an output signal proportional to the electrical signal, the amplifier circuit having multiple gains that successively increase;
    an analog to digital converter adapted to convert the output signal of the amplifier circuit to digital format;
    a gain select logic circuit to output a gain code to select the gain of the amplifier; and
    a density signal generator circuit including two LUTs, wherein the gain code is used to address the LUTs, one of the LUTs is adapted to receive the output of the analog to digital converter and produce an output density scaled to include lower order bits, the other LUT is adapted to receive the gain code and produce an output density scaled to include high order bits, and a concatenation adder of the output densities of the two LUTs to produce a summation density signal of the LUTs outputs such that the LUTs outputs form an overlap.

10. An auto-ranging densitometer as set forth in claim 9 wherein the overlap is at least about 0.02 density units.

11. A process for determining the density of a test sample, said process comprising the steps of:
    producing an amplified output signal proportional to intensity of light on a photodetector;
    converting the amplified output signal to a digital signal format;
    selecting a gain for the amplified output signal from the converted digital signal;
    employing the gain code in combination with the digital signal to produce an output density scaled to include only low order bits and to produce an output density scaled to include only high order bits, and
    concatenation adding the two output densities to produce a summation density signal.

12. The process of claim 11 wherein the step of concatenation further comprises employing the gain code as an address for a set of LUTs.

13. The process of claim 12 wherein the address has a number of bits equal to a summation of the digital signal and the gain code of the amplified output signal.

14. The process of claim 12 wherein the LUTs have an output that is combined.

15. The process of claim 14 wherein the output from the LUTs is a concatenation of outputs from the LUTs.

16. The process of claim 14 wherein the output from the LUTs is an addition of both outputs from the look up tables.

* * * * *